United States Patent

Seto et al.

[11] Patent Number: 5,830,338
[45] Date of Patent: Nov. 3, 1998

[54] COMBINATION ISE AND SOLUTIONS THEREFOR

[75] Inventors: Fung Seto, N. Grafton; Steven J. West, Hull; Xiaowen Wen, Lexington, all of Mass.

[73] Assignee: Orion Research Inc., Beverly, Mass.

[21] Appl. No.: 609,225

[22] Filed: Mar. 1, 1996

[51] Int. Cl.$^6$ .................................................. G01N 27/26

[52] U.S. Cl. ........................ 204/416; 204/418; 204/419; 204/435

[58] Field of Search .................................. 204/433, 435, 204/416, 418, 419

[56] References Cited

U.S. PATENT DOCUMENTS 3,442,782  5/1969  Schiller et al. ........................ 204/419
3,492,216  1/1970  Riseman et al. ....................... 204/419

Primary Examiner—Bruce F. Bell
Attorney, Agent, or Firm—Ernest V. Linek

[57] ABSTRACT

Described is a combination, PVC-membrane, Ion-Selective Electrode (ISE) with a replaceable sensing module and a single-junction, sleeve-type reference electrode. pH and ion-selective electrodes (ISEs) in the "Combination" configuration, i.e., single probes containing both the sensing and reference half-cells, are more convenient, more economical, and can be used to analyze smaller samples than an equivalent pair of separate half-cell electrodes.

14 Claims, 4 Drawing Sheets

5,830,338

COMBINATION ISE AND SOLUTIONS THEREFOR

BACKGROUND OF THE INVENTION

A complete potentiometric measurement cell consists of two half-cells (see FIG. 1 attached hereto). Ion-selective electrode measurement cells are potentiometric cells where one-half cell is the ion-selective electrode (ISE) and the other is the reference electrode. The reference electrode usually includes the following: an internal reference element composed of a metal or metal-salt combination; one or two reference electrolyte solutions (salt bridge solutions); and one or two liquid junctions, which are orifices, porous barriers, or other restrictions. One junction acts to prevent excessive mixing of a reference electrolyte with the test solution (sample), but at the same time provides electrical contact between that reference electrolyte and sample. This reference electrolyte may also directly contact the reference element, or may contact via a second liquid junction a second reference electrolyte. In this latter case, the second reference electrolyte contacts the reference element. ISEs and reference electrodes can be constructed as separate assemblies which are then used together in a test solution to comprise an entire measuring cell. Often, however, all of these elements are combined in a single mechanical assembly or probe and referred to as a combination ISE. Combination ISEs are advantageous in that they are often less expensive than a pair of individual half-cell electrodes, and the more compact geometry allows use in smaller volumes of sample.

SUMMARY OF THE INVENTION

The present invention is a combination ISE which has a replaceable ISE module which also forms part of the liquid junction, and a single internal reference electrolyte solution compartment. The benefits of this invention are threefold. First, the ISE module is replaceable; this is beneficial because often the ion-selective sensing membrane has the shortest useful life of all components. Second, using the ISE module to form part of the liquid junction is beneficial because it permits a preferred reference junction configuration, (an annular sleeve), to be used without geometrical compromise, and locate them both at the very tip of the probe so that a minimum immersion depth is required. Third, having a single liquid junction and reference electrolyte simplifies the mechanical construction. These concepts are best understood through reference to the drawings accompanying this specification, namely FIGS. 1, 2a, 2b and 3. It should be understood that, in use, the bottom ends of these probes, as oriented in the drawings, would be immersed in sample to a typical depth of 1 to 5 cm, and that the probes themselves are typically in the range of 12 cm long and 1 cm in diameter.

In this invention, combination probes with PVC sensing membranes were designed and evaluated for the following analyte ions: nitrate, nitrite, potassium, calcium, and magnesium. The design goals included the following features:

overall performance characteristics equivalent to or better than half-cell electrodes used with separate single- or double-junction reference electrodes;

easily replaceable ISE module;

single-junction, flowing, flushable, annular sleeve liquid junction;

ability to analyze small samples (<1M1);

reference filling solution compositions that are non-contaminating even in small sample volumes;

are optimized so as to minimize the effect of temperature in the analyte concentration ranges of principal interest: and are equitransferent, that is, they contain anions and cations with nearly equal mobilities so that liquid junction potentials are minimal.

In one especially preferred embodiment, the combination ISE of the present invention comprises in combination a tapered ISE module, the outer surface of which serves as the inner cone of the annular sleeve liquid junction. A cap and spring together provide constant tension between the inner and outer cones of the sleeve which can be flushed by a thumb-press on the cap. A threaded, hydrophobic, single or double O-ring seal connects the module to the electrode inner body.

Another embodiment of the present invention is directed to a series of reference electrolyte solutions for use with the preferred ISE, such that the following ISE modules can be used with a single reference electrolyte and junction: ammonium, barium, bromide, cadmium, calcium, chloride, cupric, cyanide, fluoride, fluoroborate, iodide, lead, lithium, magnesium, nitrate, nitrite, perchlorate, potassium, silver, sulfide, sodium, surfactant, thiocyanate, and water hardness.

DETAILED DESCRIPTION OF THE PREFERRED EMBODIMENT

As described above, and as illustrated in FIGS. 2a, 2b and 3, the present invention is directed to a combination, PVC-membrane, Ion-Selective Electrode (ISE) with a replaceable ISE module and a single-junction, annular sleeve liquid junction reference electrode. pH and ion-selective electrodes (ISEs) in the "Combination" configuration, i.e., single probes containing both the sensing and reference half-cells, are more convenient, more economical, and can be used to analyze smaller samples than an equivalent pair of separate half-cell electrodes.

In this invention, combination probes with PVC sensing membranes were designed and evaluated for the following analyte ions: nitrate, nitrite, potassium, calcium, and magnesium.

The preferred combination electrode of the present invention includes the following features:

(a) overall performance characteristics equivalent to or better than half-cell electrodes used with separate single- or double-junction reference electrodes;

(b) easily replaceable ISE module;

(c) single-junction, flowing, flushable, annular sleeve liquid junction; ability to analyze small samples (<1 mL); and (d) reference filling solution compositions that are non-contaminating even in small sample volumes, and are optimized so as to minimize the effect of temperature in the analyte concentration ranges of principal interest;

and are equitransferent, that is, they contain anions and cations with nearly equal mobilities so that liquid junction potentials are minimal.

Figure 2A:
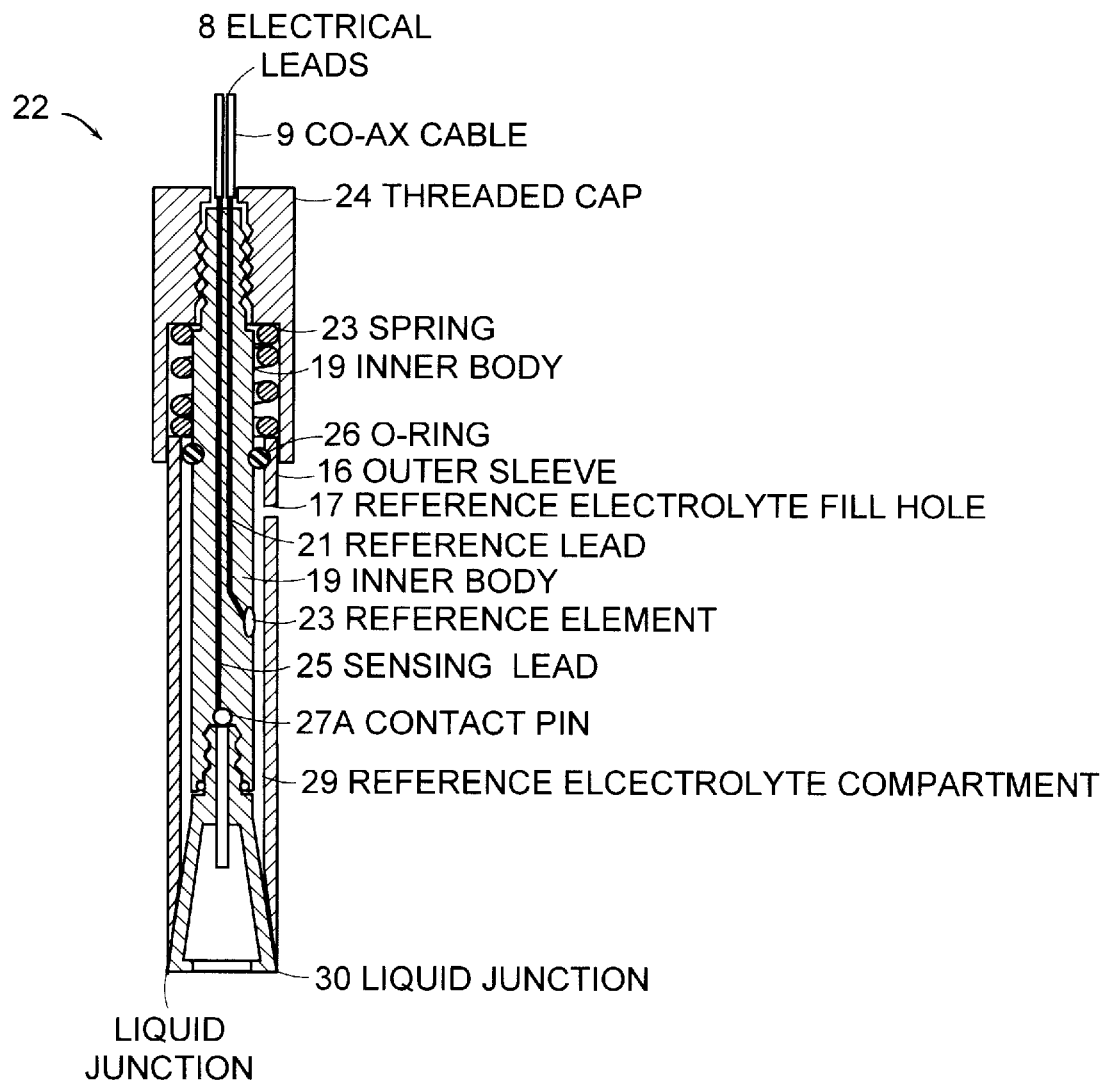
FIGS. 2a and 2b illustrates a preferred embodiment of the combination ion selective electrode (ISE) which has a replaceable ISE module which also forms part of the liquid junction, and a single internal electrolyte.
Figure 2B:
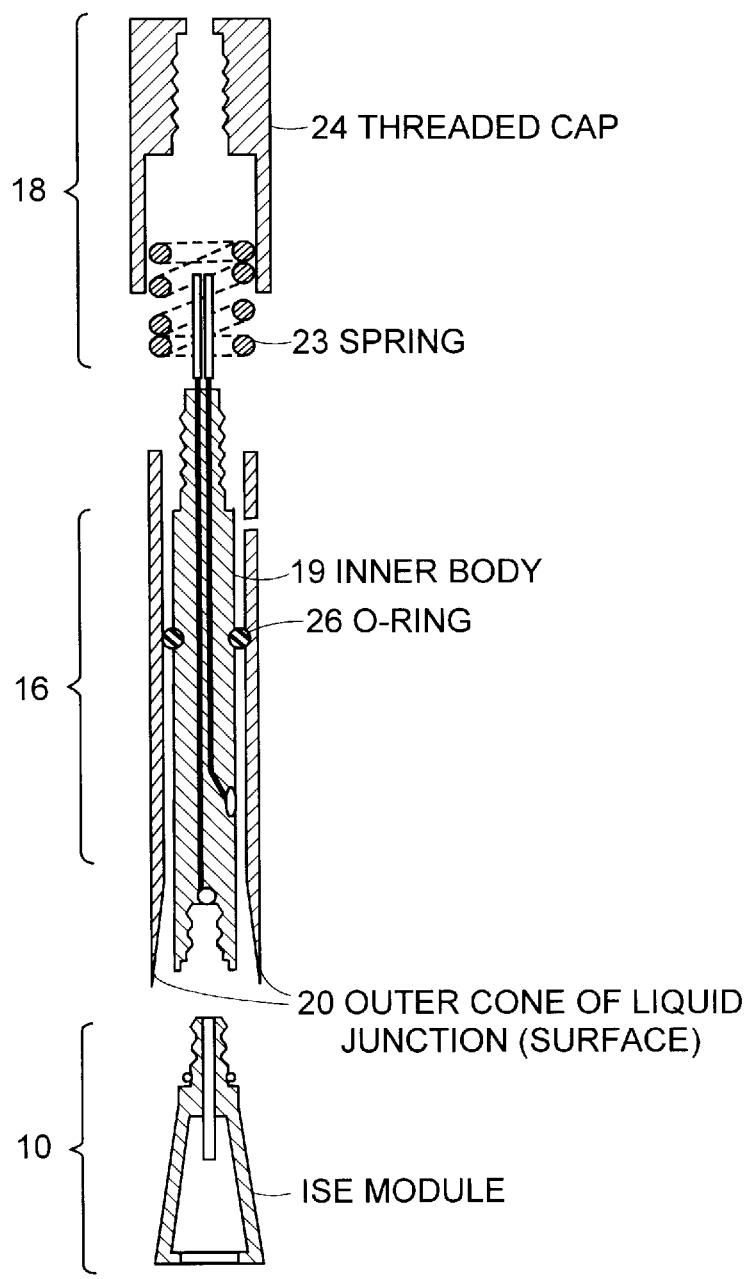
Figure 3:
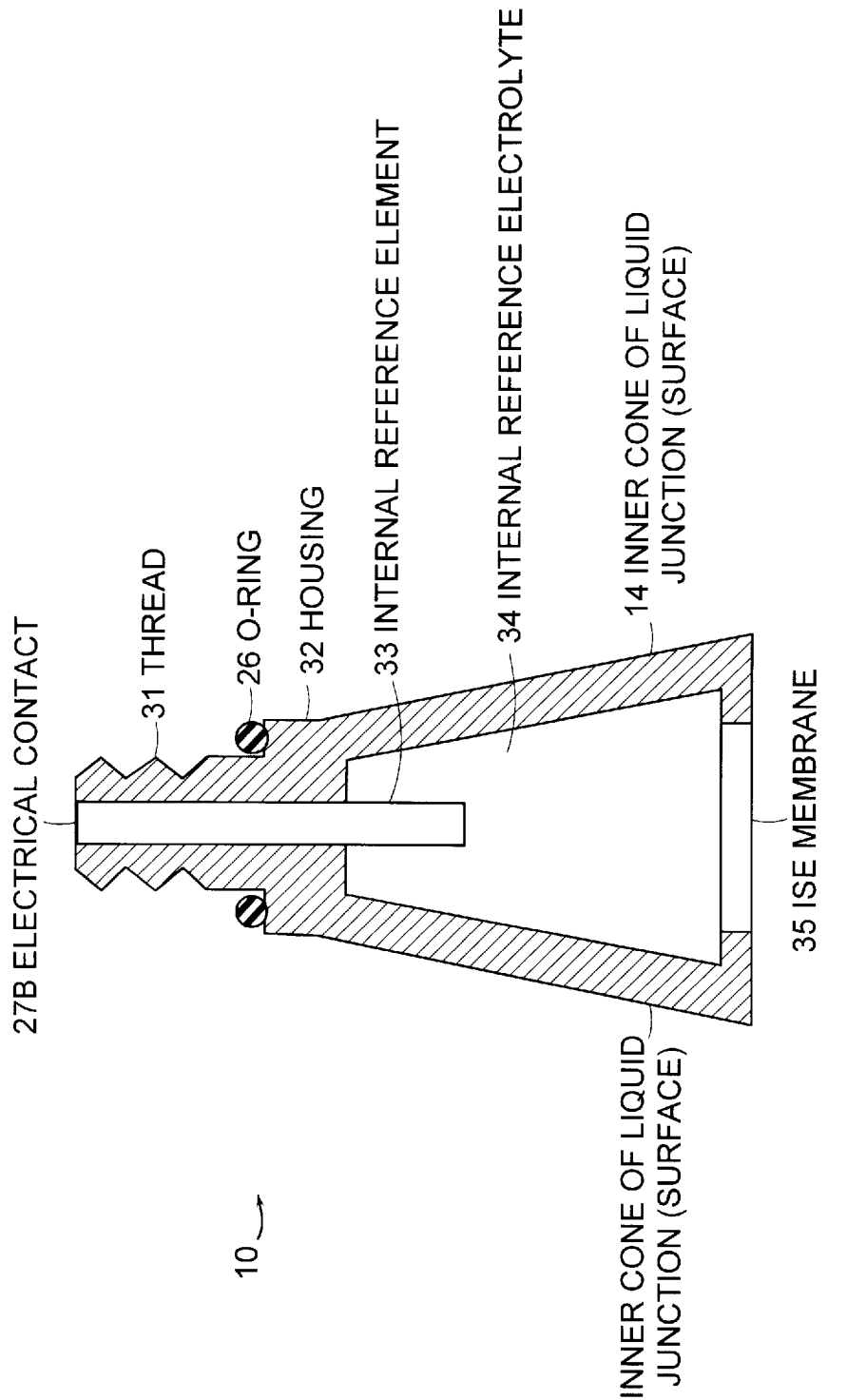
FIG. 3 illustrates a blown up version of the replaceable ISE module shown in FIG. 2b.

The preferred design of the combination electrode of the present invention is shown in detail in FIGS. 2a, 2b and 3. As illustrated, the combination electrode of this invention includes a tapered ISE module (10); the outer surface of which serves as the inner cone (14) of the annular sleeve (16). A cap and spring together (18) provide constant tension between the inner (14) and outer cones (20) of the sleeve which can be flushed by a thumb-press on the cap (24). A threaded, hydrophobic, single or double O-ring seal (26) connects the module to the electrode inner body.

Figure 1:
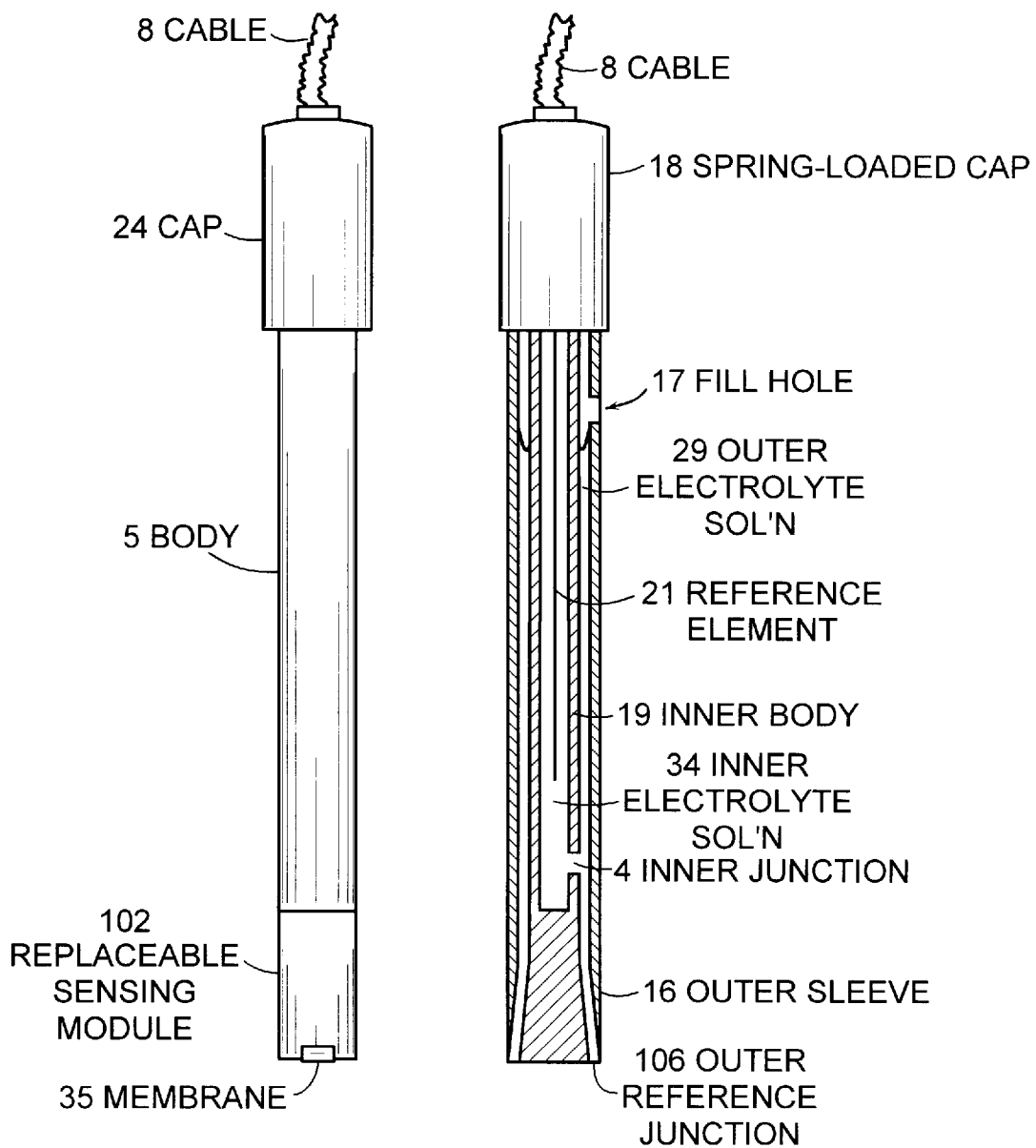
FIG. 1 shows a traditional pair of half-cell electrodes. The ISE in the drawing has a replaceable ISE module. The reference electrode is a double junction design with a annular sleeve outer junction. These electrodes represent the prior art of the present invention.

FIG. 1 shows the prior art, i.e., a pair of half-cell electrodes. The ISE (100) in FIG. 1 has a replaceable sensing module (102). The reference electrode (104) is a double junction design with a annular sleeve outer junction (106). The annular sleeve junction (106) is preferred among many types of reference junctions because of superior performance characteristics.

The combination ISE in FIGS. 2a, 2b, and 3 combine the desirable features of each of the prior art individual half-cells of FIG. 1, into a single probe with single liquid junction. The present invention is in particular, directed to the preferred means by which these individual features are incorporated into a single, functional probe. One desirable feature of the sensing half-cell is the replaceability of the ISE. There are several desirable features of the reference half-cell, including:

(1) The reference half-cell has a annular sleeve liquid junction, that is, one which is formed from an inner body which is rod-shaped with the bottom end flared into the shape of a cone. The inner body resides concentrically in an outer sleeve, which is a hollow cylinder with wall thickness sufficient to allow the inside of the bottom end to be chamfered to form a surface which mates with the cone of the inner body in the same manner as a conventional tapered glass joint. A liquid junction in the form of an annulus is thereby created between the reference electrolyte and sample solution, and the rate of flow of reference electrolyte through this junction out into the sample under the influence of gravity is controlled by the angles of the mating surfaces of the annulus and the amount of force which maintains them in contact. This force is imparted by a spring located in the electrode cap. The spring pushes the outer sleeve against the conical end of the inner body.

(2) The junction is situated at the very end of the probe body, permitting contact with the sample through immersion of the probe to a minimal depth, allowing use in small sample volumes.

(3) The reference electrolyte can be flushed through the junction by pressing the spring-loaded cap while holding the outer sleeve fixed. This action forces the inner body downward relative to the sleeve as oriented in the drawing, thereby widening the annulus and allowing greater flow.

(4) The reference electrolyte can be replenished through a fill hole located near the top of the outer sleeve.

(5) The reference electrolyte does not interfere with operation of the sensing membrane, although it does flow into the sample at a finite rate, allowing species it contains to come in contact with the membrane. In the reference half-cell shown in FIG. 1, contamination is avoided by means of a double-junction design, a concept familiar in electrochemistry. Certain species must be present in an electrolyte in order for a stable potential to be established at a reference element. Sometimes these species can interfere with the sensing membrane when they flow with the electrolyte into the sample. Therefore, two reference electrolytes are used. The inner electrolyte contains those species necessary for establishment of this reference potential. This solution communicates with an outer electrolyte via an inner liquid junction, which could be a small hole or a plug of porous, inert material such as porous ceramic. The outer electrolyte contains species which are effective in maintaining a stable junction potential at both the inner and outer junctions, but need not contain species which establish the reference element potential and which may also interfere with membrane function.

In the combination ISE shown in FIGS. 2a, 2b, and 3, only one electrolyte is used. It contains species which establish a stable reference element potential and a stable junction potential. In order to avoid interference with the sensing membrane when a variety of ion-selective membranes are used, a variety of internal reference electrolytes are used. Preferred electrolytes include those shown on Table 1;

TABLE 1

Summary of Orion Optimum Results Reference Filling Solutions

| ISEs | | |
|---|---|---|
| $Cd_{2+}$ | 1.7 M $KNO_3$ | equitransferent RFS for the specified S/J |
| $CA^{2+}$ | 0.64 M KCl | combination ISEs resulting in small |
| F | 0.06 M NaCl sat, W/ AgCl Triton X-100 0.002% | temperature coefficients and insignificant contaminations to the sample. |
| $Pb^{2+}$ | 1 M $KNO_3$ | nearly equitransferent RFS for the |
| $Ag/S^{2-}$ | 0.02 M KCl | specified S/J combination ISEs |
| $Cl^-$ | sat. w/ AgCl | with the optimum composition |
| $CN^-$ | Triton X-100 0.01% | for small temperature coefficients, small contaminations to the samples, the electrode surfaces and the junction. |
| $Ag^+/S^{2-}$ | 1 M $KNO_3$ 0.001 M AgCl | nearly equitransferent RFS for the specified S/J/ combination ISE with minimum temperature coefficient. |
| $Cu^{2+}$ | 1 M $KNO_3$ | nearly equitransferent, silver free RFS |
| $Br^-$ | 0.001 M AgCl | for the specified S/J combination |
| $I^-$ | | IDEs with minimum temperature coefficients and contaminations. |
| $K^+$ | 1 M NaCl sat. w/AgCl | RFS for the specified S/J combination ISE with optimum composition for small temperature coefficient, small contamination, and stable junction potential. |
| $NO_3^-$ | 2 M $(NH_4)_2SO_4$ | RFS for the specified S/J combination |
| $NO_2^-$ | 0.001 M NaCl sat. w/ AgCl | ISEs for reduced temperature coefficients, sample contaminations, and stable junction potential. |

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A combination ion selective electrode (ISE) comprising a replaceable ISE module which also forms part of the liquid junction, and a single internal electrolyte solution compartment.

2. The combination ISE of claim 1, wherein the outer surface of the replaceable sensing module serves as the inner cone of an annular sleeve liquid junction.

3. The combination ISE of claim 2, wherein the liquid junction comprises an annular sleeve formed by an inner cone on the ISE module which mates with an outer cone on the inside of the moveable outer sleeve.

4. A combination ion selective electrode (ISE) comprising in combination:
   (a) a reference half-cell which includes an annular sleeve junction, formed from an inner body which is rod-shaped with the bottom end of said inner body flared into the shape of a cone,
   (b) wherein said inner body resides concentrically in an outer sleeve, which is a hollow cylinder with a wall thickness sufficient to allow the inside of the bottom end of said outer sleeve to be chamfered to form a surface which mates with the cone shape of the inner body;
   (c) thereby creating a liquid junction in the form of an annular sleeve between the reference electrolyte and sample solution, and wherein the rate of flow of reference electrolyte through this junction out into the sample under the influence of gravity is controlled by the angles of the mating surfaces of the inner body and outer body sleeves and the amount of force which maintains them in contact.

5. The combination ISE of claim 4, further comprising an electrode cap and spring at the top of said outer sleeve, said cap and spring providing means for pushing the outer sleeve against the conical end of the inner body.

6. The combination ISE of claim 4, further comprising only one reference electrolyte.

7. The combination ISE of claim 6, wherein the reference electrolyte contains species necessary for establishment of a stable reference potential.

8. The combination ISE of claim 7, wherein the reference electrolyte contains species which are effective in maintaining a stable junction potential.

9. The combination ISE of claim 8, wherein the reference electrolyte is an aqueous solution consisting essentially of 1.7M $KNO_3$, 0.64M KCl, 0.06M NaCl, saturated with AgCl and containing Triton X-100 at 0.002% by weight.

10. The combination ISE of claim 8, wherein the reference electrolyte is an aqueous solution consisting essentially of 1M $KNO_3$, 0.02M KCl, saturated with AgCl and containing Triton X-100 at 0.002% by weight.

11. The combination ISE of claim 8, wherein the reference electrolyte is an aqueous solution consisting essentially of 1M $KNO_3$ and 0.001M AgCl.

12. The combination ISE of claim 8, wherein the reference electrolyte is an aqueous solution consisting essentially of 1M $KNO_3$ and 0.001M NaCl.

13. The combination ISE of claim 8, wherein the reference electrolyte is an aqueous solution consisting essentially of 1M NaCl saturated with AgCl.

14. The combination ISE of claim 8, wherein the reference electrolyte is an aqueous solution consisting essentially of 2M $(NH_4)_2SO_4$, 0.001M NaCl, saturated with AgCl.

* * * * *